United States Patent [19]
Chung

[11] Patent Number: 5,391,568
[45] Date of Patent: Feb. 21, 1995

[54] INHIBITION OF LUNG TUMORIGENESIS BY ADMINISTRATION OF A POLYPHENOL

[75] Inventor: Fung L. Chung, Yorktown Hts., N.Y.

[73] Assignee: American Health Foundation, New York, N.Y.

[21] Appl. No.: 912,157

[22] Filed: Jul. 10, 1992

[51] Int. Cl.$^6$ ............................................. A61K 31/35
[52] U.S. Cl. ................................................... 514/456
[58] Field of Search ........................................ 514/456

[56] References Cited
PUBLICATIONS

Fujita et al., Japanese J. Cancer Res, 80:503–5054, 1989.
Dietrich Hoffmann, et al., Crit. Rev. Toxicol., 21: 305–311 Naylor Dana Institute for Disease Prevention–1991 (AHF, Valhalla, N.Y., USA) "Nicotine-Derived N-Nitrosamines (TSNA) and Their Relevance in Tobacco Carcinogenesis".
Fung Lung Chung, et al., Cancer Res. 52: in press American Health Foundation-May 1, 1992 (Valhalla, N. Y.) "New Potential Chemopreventive Agents For Lung Carcinogenesis Of Tobacco Specific Nitrosamine".
Mark A. Morse, et al., Cancer Res., 50: 2613–2617 Section of Nucleic Acid Chemistry-May 1 1990 (AHF, Valhalla, N. Y. USA) "Effects of Indol–3–Carbinol on Lung Tumorigenesis and DNA Methylation Induced by 4-(Methylnitrosamino)-1-(3-Pryidyl)-1-Butanone (NNK and on the Metabolism and Disposition of NNK in A/J Mice".
Stephen S. Hecht, et al., Carcinogenesis, 10: 1901–1904 American Health Foundation-1989 (Vahalla, N. Y., USA) "Rapid Single-Dose Model for Lung Tumor Induction in A/J Mice by 4-(Methylnitrosamino)-1-(-3-Pyridyl)-1-Butanone and the Effect on Diet".
E. Wynder, et al R. Sasaki and K. Aoki (eds.), Epidomiology and Prevention of Cancer, pp. 103–127. Nagayo, Japan: University of Nagoya Press, 1990. American Health Foundation (New York, USA) Institute of Preventive Oncology (Tokyo, Japan) Department of Field Research, Center for Adult Disease (Osaka, Japan) "Comparative Epidemiology of Cancer Between the United States and Japan: A Second Look".
Zhi Y. Yang, et al., Carcinogenesis, 10: 411–415 Department of Dermatology–1989 (Cleveland, Ohio, USA) "Protection Against Polycyclic Aromatic Hydrocarbon–Induced Skin Tumor Initiation in Mice by Green Tea Polyphenols".
Han Chi and Xu Yong Biomedical and Environmental Science, 3: 35–42, Chinese Academy of Preventive Medicine–Apr. 21, 1989 (Beijing, China) "The Effects of Chinese Tea on Occurrence of Esophageal Tumor Induced by N-Nitrosomethylbenzylamine in Rats".
Tsuneo Kada, et al., Mutat. Res., 150: 127–132 National Institute of Genetics–1985 (Shizuoka-ken, Japan) "Detection and Chemical Identification of Natrual Bio–Antimutagens
Yoshihiro Fujita, et al Japanese J. Cancer Res., 80:503–505 Department of Surgery, Fukuchlyama National Hospital-Jun. 1989 (Japan) "Inhibitory Effect of (−)-Epigallocatechin Gallate on Carcinogenesis With N-Ethyl-N'-Nitro-N-Nitrosaguanidine in Mouse Duodenum".
Z. Y. Yang, et al., Proc. Amer. Assoc. Cancer Res., Res., 32: 125, 1991 Inhibition of N-nitrosodiethylamine (NDEA)-induced lung and forestomasch tumorigenesis in A/J mice by green tea.

(List continued on next page.)

Primary Examiner—Jerome D. Goldberg
Attorney, Agent, or Firm—Ladas & Parry

[57] ABSTRACT

A method is provided for reducing the incidence of lung cancer in a mammal by administering thereto a pharmacologically effective amount of epigallocatechin gallate (EGCG). The EGCG may be administered to the mammal in the form of drinking water and particularly in the form of, for example, 2% green tea. The EGCG may be isolated prior to administering the same and is subsequently put into solution for administration thereof. The EGCG is an antioxidant.

4 Claims, 2 Drawing Sheets

PUBLICATIONS

Fung Lung Chung, et al Carcinogenesis, 6: 539–543 Division of Chemical Carcinogenesis, Naylor Dana Institute for Disease Prevention–1985 (AHF, Valhalla, N. Y., USA) "Effects of Dietary Indoles and Isothiocyanates on N–Nitrosodimethylamine and 4–(Methyl-Nitrosamino)-1-(3-Pyridyl)-1-Butanone-Hydroxylation and DNA Methylation in Rat Liver".

Fung Lung Chung, et al Carcinogenesis, vol. 13, No. 7. Division of Chemical Carcinogenesis–Mar. 26, 1992 (AHF, Valhalla, N. Y., USA) "Increased 8-Oxodeoxybuanosine Levels in Lung DNA of A/J Mice and F344 Rats Treated With the Tobacco-Specific Nitrosamine 4-(Methylinitrosamine)-1-(3-Pyridyl)-1-Butanone".

Stephen S. Hecht, et al Beitr. Tabakforsch., 9:1–6 American Health Foundation–Apr. 1977 (Valhalla, N.Y., USA) "Chemical Studies on Tobacco Smoke".

Hiroshi Kasi and Susumi Nishimura Nucleic Acids Res., 12: 2137–2145 National Cancer Center Research Institite–Jan. 31, 1984 (Tokyo, Japan) "Hydroxylation of Deoxybuanosine at the C-8 Position by Ascorbic Acid and Other Reducing Agents".

Robert A. Floyd, et al Free Radical Res. Commun., 1: 163–172, 1986 Oklahoma Medical Research Foundation–Jun. 16, 1985 (Oklahoma City, Okla., USA) "Hydroxyl Free Radical Adduct of Deoxyguanosine: Sensitive Detection and Mechanisms of Formation".

Harold N. Graham, In: G. A. Spiller (ed.), The methylxanthine beverages and foods. Chemistry, Consumption and Health Effects, pp. 29–74 Alan R. Liss, Inc.–1984 (New York, N. Y., USA) "Tea: The Plant and its Manufacture; Chemistry and Consumption of the Beverage".

Randall J. Ruch, et al Carcinogenesis, 10: 1003–1008 Dept. of Pathology & Pharmacology & Experimental Therapeutics–1989 (Toledo, Ohio) and Cancer Institute, Chinese Academny of Sciences (Beijing, China) "Prevention of Cytotoxicity and Inhibition of Intercellular Communication by Antioxidant Cathechins Isolated from Chinese Green Tea".

T. Osawa, et al 52: 139–153 Basic Life Science, 1990 (Japan).

Wang, et al., "Inhibitory effect of orally administered green tea on ultraviolet B light (UV-B)–induced carcinogenesis on skin of SKH-1 mice" Proceedings of the American Association of Cancer Research–vol. 32. Mar. 1991, 129 Carcinogenesis.

Dietrich Hoffmann, et al Cancer Res., 45: 935–944 Naylor Dana Institute for Disease Prevention–Mar. 1985 (AHF Valhalla, N. Y., USA) "Nicotine–Derived N-Niotrosamines and Tobacco–Related Cancer: Current Status and Future Directions".

Lucienne Lagopoulos, et al Carcinogenesis vol. 12, No. 2 pp. 211–215, 1991 Nestec Ltd.–1991 (Switzerland) "The Correlation of Body Growth With Diethylnitrosamine–Induced Hepatocarcinogenesis in Relation to Serum Insulin and Somatomedin–C".

L. VanderPloeg, et al Cancer Research 51.3399–3404, Jul. 1, 1991 Departments of Pharmacology & Toxicology–Jul. 1, 1991 (E. Lansing, Mich., USA) "Influence of Caffeine on Development of Benign and Carcinomatous Mammary Gland Tumors in Female Rats Treated With Carinogens 7,12–Dimethylbenz(A)Anthracene and N–Methyl-N-Nitrosourea".

S. Belinsky, et al Cancer Res., 50: 3772–3780 Laboratory of Molecular Toxicoloty–Jun. 15, 1990 (N. Carolina, USA) "Dose–Response Relationship Between $O^6$-Methylguanine Formation in Clara Cells and Induction of Pulmonary Neoplasia in the Rat by 4-(Methylnitrosamino)—1-(3-pyridyl)–butanone".

Lisa A. Peterson, et al Cancer Res., 51: 5557–5564 Division of Chemical Carcinogenesis–Oct. 15, 1991 (AHF, Valhalla, N. Y., USA) "$O^6$-Methylguanine is a Critical Determinant of 4-(Methylnitrosamino)-1-(3-Pyridyl)-1-Butanone Tumorigenesis in A/J Mouse Lung".

Theodora R. Devereus, et al Carcinogenesis, 12: 299–303 Laboratory of Molecular Toxicology–1991 (Research Triangle Park, N. C., USA) "Role of Ras Protooncogene Activation in the Formation of Spontaneous and Nitrosamine-Induced Lung Tumors in the Resistant C3H Mouse".

Chen, et al., Chinese Journal–Oncology, 9: 109–111, 1987. "Effect of six edible plants on the development of $AFB_1$–induced s-glutamyl transpeptidase positive hepatocyte foci in rats".

Marur, J. J. Mol. Biol., 3: 208–216, 1961. "A procedure for the isolation of deoxyribonucleic acid from microorganisms".

Matsuzaki, et al., Nippon Nogeigaku Kaishi, 59: 129–134, 1985, "Antioxidative activity of tea leaf catechins".

Takino, et al., Japanese Patent, 59: 26385, 1984.

International Agency for Research on Cancer. "Tobacco Smoking", IARC, Lyon, France, 1986, vol. 38.

(List continued on next page.)

PUBLICATIONS

Shigeru Yoshizaza, et al; Takashi Yoshida, et al and Takashi Sugimura Phytotherapy Research, vol. 1, No. 1, 1987 National Cancer Research Institute (Tokyo, Japan); Faculty of Pharmaceutical Sciences, Okayama University (Okayama, Japan) and National Cancer Center (Tokyo, Japan) "Antitumor Promoting Activity of (−) Epigallocatechin Gallate, the Main Constituent of 'Tannin' in Green Tea".

Mark A. Morse, et al., Cancer Research 49, 1894–1897 Division of Chemical Carcinogenesis–Jun. 1, 1989 (AHF, Valahlla, N. Y., USA) "Effects of Aromatic Isothiocyanates on Tumorigenicity, $O^6$–Methylguanine Formation, and Metabolism of the Tobacco–Specific Nitrosamine 4–(Methylnitrosamino)–1–(3–Pyridyl-)–1–Butanone in A/J Mouse Lung".

P. Pepin, et al The Cancer Journal, vol. 3, No. 5, pp. 266–273 Laboratory of Cancer Etiology & Chemoprevention–Sep./Oct. 1990 (Quebec City, Canada) "Inhibition of NNK–Induced Lung Tumorigenesis in A/J Mice by Ellagic Acid and Butylated Hydroxyanisole".

Stephen S. Hecht, et al Carcinogenesis, vol. 9, No. 1, pp. 161–165 Division of Chemical Carcinogenesis–1988 (AHF, Valhalla, N. Y., USA) "Evidence for 4–(-3–Pyridyl(–4–Oxobutylation of DNA in F344 Rats Treated with the Tobacco–Specific Nitrosamines 4–(Methylnitrosamino)–1–(3–Pyridyl)–1–Butanone and N′–Nitrosonornicotine".

Rothwell, K., Nature vol. 252, pp. 69–70, Nov. 1, 1974 "Dose-related inhibition of chemical carcinogenesis in mouse skin by caffeine".

Kakunaga, T., Nature, vol. 258, pp. 248–250, Nov. 20, 1975 "Caffeine inhibits cell transformation by 4–nitroquinoline–1–oxide".

Nomura, T., Nature, vol. 260, pp. 547–549, Apr. 8, 1976 "Diminution of tumorigenesis intitiated by 4–nitroquinoline–1–oxide by post-treatment with caffeine in mice".

Caffeine (-) Epigallocatechin-3-gallate (EGCG)

INHIBITION OF LUNG TUMORIGENESIS BY ADMINISTRATION OF A POLYPHENOL

FIELD OF THE INVENTION

This invention relates to treatment for the inhibition of lung tumorigenesis by the administration of a pharmaceutical compound and to the pharmaceutical compound which is administered.

BACKGROUND

It has been noted that the lung cancer mortality among males in Japan is substantially lower than that in the United States, even though cigarette smoking has been substantially more prevalent in Japan than in the United States for the past 40 years. Although diet may be an important factor, other factors such as race and smoking patterns may play a role as well.

SUMMARY OF INVENTION

It is an object of the invention to provide a method for reducing the incidence of cancer in a mammal and particularly where the cancer is 4-(methylnitrosamino)1-(3 pyridyl)-1-butanone (NNK) lung tumorigenesis. NNK is a tobacco-specific nitrosamine.

It is another object of the invention to provide for a pharmacological treatment of mammals to provide in turn for reducing the incidence of lung tumors and specifically lung tumors induced by exposure to NNK.

Still another object of the invention is to provide an isolated pharmacological product capable of being administered as a treatment to inhibit the incidence of cancer induced by exposure to cigarette smoke or the like.

In achieving the above and other objects of the invention, there is provided, in accordance therewith, a method which comprises reducing the incidence of cancer in a mammal by administering to the mammal a pharmacologically effective amount of a polyphenol such as epigallocatechin gallate (EGCG). The method is particularly applicable where the cancer is NNK induced lung tumorigenesis. The EGCG is preferably administered according to the invention to the mammal during and after the same period in which the NNK is administered to the animal, or in other words, in which the mammal is exposed to the NNK.

In accordance with a further aspect of the invention, the EGCG may preferably be administered to the mammal in the form of drinking water or as approximately 2% green tea. The EGCG may furthermore be administered in doses in the order of magnitude of about 560 ppm.

The invention may be more specifically regarded as inhibiting the formation of 8-OH-dG in lung DNA. As will be shown hereinbelow, the mammal may preferably be maintained at 20°±2° centigrade and at a relative humidity of about 50±10%.

The above and other objects, features and advantages of the invention will be found in the following detailed description as illustrated in the accompanying drawing:

DETAILED DESCRIPTION

Figure 1:
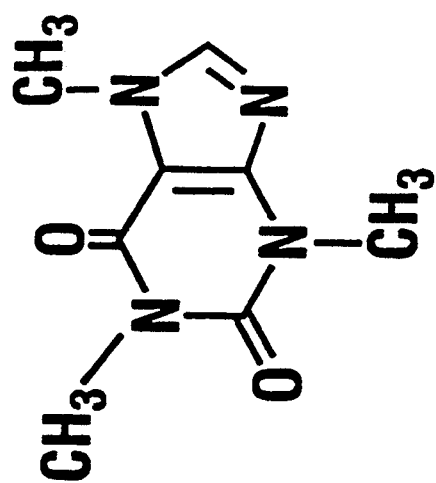
FIG. 1 illustrates the structures of some compounds referred to in the description which follows hereinafter.
Figure 1:
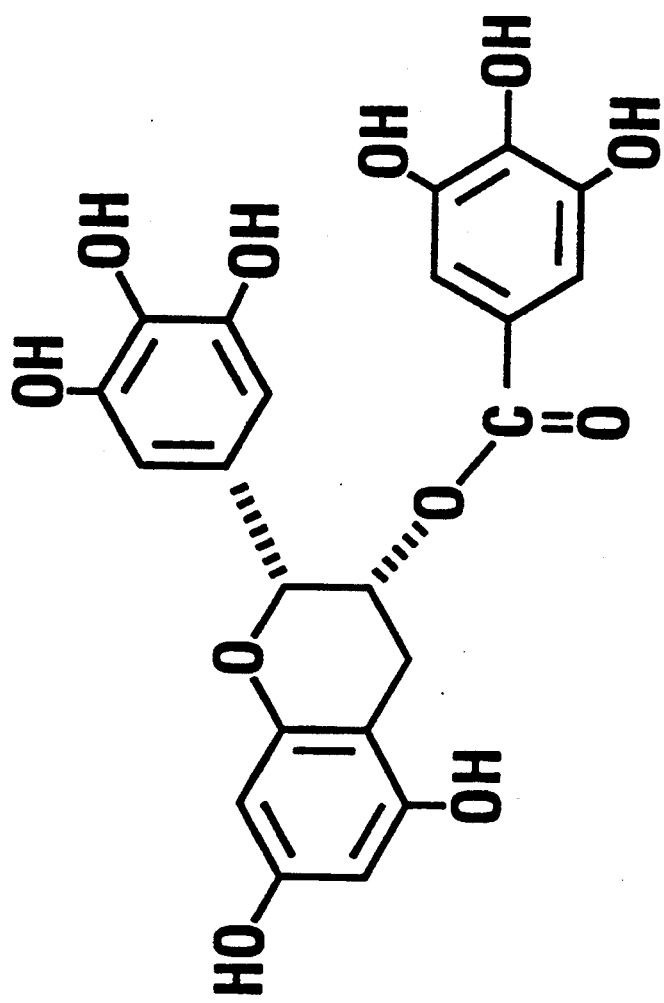

In the development of this invention, the effects of green tea, its major polyphenol or component (-)-epigallocatechin gallate (EGCG), and caffeine on the tobacco-specific nitrosamine 4-(methylnitrosamino)1-(3-pyridyl)1-butaone (NNK)-induced lung tumorigenesis in A/J mice were examined. The effects of green tea and EGCG on $O^6$-methylguanine ($O^6$-mG) and 8-hydroxydeoxyguanosine (8-OH-dg) formation in lungs caused by NNK treatment were also considered.

Mice were given 2% tea, 560 ppm EGCG, in solution in drinking water for 13 weeks. During this time, NNK (11.65 mg/kg b.w.) was administered by gavage three times weekly for 10 weeks from weeks 3 to 12. The bioassay was terminated 6 weeks after the last NNK treatment. Mice treated with NNK developed 22.5 lung adenomas per mouse, whereas NNK treated mice that drank green tea or EGCG as drinking water developed only 12.2 ($p<0.01$) and 16.1 ($p<0.05$) tumors per mouse, respectively.

Mice that drank green tea or caffeine solution showed lowered body weight gains, although little difference in water and diet consumption was noted in these groups. While green tea and EGCG exerted little effect on the formation of $O^6$-mG, a critical DNA lesion in NNK lung tumorigenesis, both treatments suppressed the increase of 8-OH-dG levels in mouse lung DNA. The inhibition of 8-OH-dG formation in lung DNA by green tea and EGCG is consistent with their ability to inhibit lung tumorgenesis by NNK. Because 8-OH-dG is a DNA lesion caused by oxidative damage, these results suggest that the mechanism of inhibition by green tea and EGCG in NNK-induced lung tumorgenesis is due at least partly to their antioxidant properties.

Among the carcinogens found in cigarette smoke, 4-(methylnitrosamino)-1-(3-pyridyl)1-butaone (NNK) appears highly specific for lung cancer induction in various laboratory animals. Hoffmann, D., Rivenson, A., Chung, F. -L. and Hecht, S. S. Nicotine-derived N-nitrosamine (TSNA) and their relevance in tobacco carcinogenesis. Crit. Rev. Toxicol., 21: 305–311, 1991; International Agency for Research on Cancer. Tobacco Smoking. IARC, Lyon, France, 1986, Vol. 38. NNK is also one of the most potent carcinogenic nitrosamines found in tobacco. International Agency for Research on Cancer. Tobacco Smoking. IARC, Lyon, France, 1986, Vol. 38. These activities suggest that NNK may play a significant role in the development of lung cancer in smokers. Our studies showed that dietary compounds such as isothiocyanates and indoles in cruciferous vegetables inhibited lung tumor induction in rats and mice treated with NNK. Chung, F. -L., Morse, M. A., and Eklind, K. I. New potential chemopreventive agents for lung carcinogenesis of tobacco-specific nitrosamine. Cancer Res., 52: in press, 1992; Morse, M. A., LaGreca, S. D., Amin, S. G., and Chung, F. -L. Effects of indole-3-carbinol on lung tumorigenesis and DNA methylation induced by 4-(methylnitrosamino)1-(3-pyridyl)1-butanone (NNK) and on the metabolism and disposition of NNK in A/J mice. Cancer Res., 50: 2613–2617, 1990. Furthermore, NNK-treated mice fed a cereal-based diet (NIH-07) developed significantly less lung tumors than those fed the semipurifed diet (AIN-76A). Hecht, S. S., Morse, M. A., Amin, S. G., Stoner, G. D., Jordan, K. G., Choi, C. -I., and Chung, F. -L. Rapid single dose model for lung tumor induction in A/J mice by 4-(methylnitrosamino)1-(3-pyridyl)-1 butanone and the effect of diet. Carcinogenesis, 10: 1901–1904, 1989. These results indicate that NNK-induced lung carcinogenesis is influenced by diet.

Epidemiological studies have shown that lung cancer mortality among males in Japan is considerably lower than that in the United States, even though the prevalence of cigarette smoking during the last 40 years among Japanese males is much higher than in the United States. Wynder, E. L., Fujita, Y., Harris, R. E., Hiraguma, T., and Hiyarnor, T., Comparative epidemiology of cancer between the United States and Japan: a second look. In: R. Sasaki and K. Aoki (eds.), Epidemiology and Prevention of Cancer, pp. 103–127. Nagoya, Japan: University of Nagoya Press, 1990. Diet could be an important factor contributing to the difference in lung cancer risk between these two countries, although other factors such as race and smoking patterns may also be involved. Considering the dietary differences between these two countries, the prevalence of green tea consumption in Japan is an intriguing one because numerous studies have shown that green tea and its polyphenol extract inhibited mutagenesis and carcinogenesis. Wang, Z. Y., Khan, W. A., Bickers, D. R., and Mukhtar, H. Protection against polycyclic aromatic hydrocarbon-induced skin tumor initiation in mice by green tea polyphenols. Carcinogenesis, 10: 411–415, 1989; Han, C. and Xu, Y. The effect of Chinese tea on occurrence of esophageal tumor induced by N-nitrosomethylbenzylamine in rats. Biomedical and Environmental Science, 3: 35–42, 1990; Kada, T., Kaneko, K., Matsuzaki, S., Matsuzaki, T., and Hara, Y. Detection and chemical identification of natural bio-antimutagens, a case of the green tea factor. Mutat. Res., 150: 127–132, 1985; Fujita, Y., Yamane, T., Tanaka, M., Kuwata, K., Okuzumi, J., Takahashi, T., and Fujiki, H. Inhibitory effect of (-)-epigallocatechin gallate on carcinogenesis with N-ethyl-N'-nitro-N-nitrosoguanidine in mouse duodenum. Japanese J. Cancer Res., 80:503–505, 1989; Wang, Z. Y., Huang, M. T., Hong, J. -Y., Conney, A. H., and Yang, C. S. Inhibition of N-nitrosodiethylamine (NDEA)-induced lung and forestomach tumorigenesis in A/J mice by green tea. Proc. Amer. Assoc. Cancer Res., 32: 125, 1991.

In order to assess the possible role of green tea in protection against lung cancer, the effects of green tea and its major components, (-)- epigallocatechin gallate (EGCG) and caffeine (structures in FIG. 1) on the NNK-induced lung tumorigenesis in A/J mice were examined. In addition, a study was made of the effects of green tea and EGCG on liver and lung $O^6$-methylguanine ($O^6$-mG) and 8-hydroxydeoxyguanosine (8-OH-dG) formation (both are DNA lesions caused by NNK treatment. Chung, F. -L., Wang, M., and Hecht, S. S. Effects of dietary indoles and isothiocyanates on N-nitrosodimethylamine and 4-(methylnitrosamino)-1-(3-pyridyl)1-butanone a-hydroxulation and DNA methylation in rat liver. Carcinogenesis, 6: 539–543, 1985; Chung, F. -L. and Xu, Y. Increased 8-hydroxydeoxyguanosine in DNA of mice and rats treated with the tobacco-specific nitrosamines 4-(methylnitrosamine)1-(3-pyridyl)1-butanone., in press, carcinogenesis 1992.

MATERIALS AND METHODS

Chemicals

NNK was synthesized by a known method. Hecht, S. S., Chen, C. B., Dong, M., Ornaf, R. M., Hoffmann, D., and Tso T. C. Studies on non-volatile nitrosamines in tobacco. Beitr. Tabakforsch., 9:1–6, 1977. Green tea was procured from the Tea Research Institute of the Chinese Academy of Agricultural Sciences in Hangzhou, China and stored in a sealed plastic bag at 4° C. before use. EGCG was obtained by fractionation of a crude catechin mixture, which was prepared from green tea by a method described by Matsuzaki and Hara, Matsuzaki, T. and Hara, Y. Antioxidative activity of tea leaf catechins. Nippon Nogeigaku Kaishi, 59: 129–134, 1985; using Sephadex LH-20 (Pharmacia, Inc.) column chromatography according to a method described by Takino, et al. Takino, Y., Tanizawa, H., Ikeda, H., and Fujiki, S. Japanese Patent, 59: 26385, 1984. The purified EGCG was stored at −20° C. and its purity was determined to be greater than 99% by HPLC (high-performance liquid chromatography) analysis. Caffeine was purchased from Sigma Chemical Co. (St. Louis, Mo.).

A 2% tea was prepared daily by adding 50 ml of boiling water to 1 g of green tea leaves followed by filtration after standing at room temperature for 30 minutes. The concentrations of EGCG and caffeine in the tea infusion were determined by a reverse phase HPLC described below. EGCG and caffeine solutions were prepared daily with tap water. The concentrations of EGCg and caffeine, 560 ppm and 1120 ppm respectively, were identical to those found in the tea. $O^6$-mG was purchased from Chemsyn Science Laboratories (Lenexa, Kans.). Guanine, deoxyguanosine, nuclease P1, ribonuclease A, alkaline phosphatase (type III), and proteinase K were purchased from Sigma Chemical Co. 8-OH-dG, prepared by the method of H. Kasai and S. Nishimura (Kasai, H. and Nishimura, S. Hydroxylation of deoxyguanosine at the C-8 position by ascorbic acid and other reducing agents; Nucleic Acids Res., 12: 2137–2145, 1984) was purified by HPLC as described by Floyd, et al; Floyd, R. A., Watson, J. J., Wong, P. K. Altmiller, D. H., and Rickard, R. C. Hydroxyl free radical adduct of deoxyguanosine: sensitive detection and mechanism of formation. Free Radical Res. Commun., 1: 163–172, 1986.

Concentrations of EGCG and caffeine in tea were determined on a Varian 5000 HPLX system and a Varian 2050 UV detector (Sunnyvale, Calif.) using a Whatman Partisil-50DS-2 column (Clifton, N.J.) eluted isocratically with $H_2O$/dimethyl formamide/acetic acid/acetonitrile (81/15/3/1) at a flow rate of 1.0 ml/min. $O^6$-mG was analyzed using a HPLC system coupled to a Perkin Elmer LS40 fluorescence detector (Norwalk, Conn.) and a LC290 UV spectrophotometric detector as reported in Chung, F. -L., Wang, M., and Hecht, S. S. Effects of dietary indoles and isothiocyanates on N-nitrosodimethylamine and 4-(methylnitrosamino)-1-(3-pyridyl)1-butanone a-hydroxulation and DNA methylation in rat liver; Carcinogenesis, 6: 539–543, 1985. The HPLC system consists of a Perkin Elmer binary LC pump 250 and two Whatman Partisil-10 SCX (25×0.45 cm) columns eluted with ammonium phosphate buffer in 10% methanol (0.1M, pH 2.0) at a flow rate of 2.0 ml/min. Analysis of 8-OH-dG was performed on a HPLC system connected to a Model 1111B UV detector and a Model LC17A/LC-4B amperometric detector from Bioanalytical Systems (BAS, West Lafayette, Ind.), set at 1.0 nA range, +600 mV (Chung, F. -L. and Xu, Y. Increased 8-hydroxydeoxyguanosine in DNA of mice and rats treated with the tobacco-specific nitrosamines 4-(methylnitrosamine)-1-(3-pyridyl)1-butanone., in press, carcinogenesis, 1992). The HPLC system consists of a Waters Model 510

HPLC pump equipped with a Waters Model U6K injector (Milford, Mass.). The column used was a 0.46×25 cm Altex Ultrasphere ODS column (Beckmann Instruments Inc., Berkely, Calif.) protected with a $C_{18}$ guard column (Alltech Associates, Inc., Deerfield, Ill.). The eluant was a 10% aqueous methanol containing 12.5 mM citric acid, 25 mM sodium acetate, and 10 mM acetic acid, (pH 5.1) and run at a flow rate of i ml/min. Guanine was quantitated with the HPLC-UV detection.

Six-week old female A/J mice were purchased from Jackson Labs (Bar Harbor, Maine) and kept under quarantine for 2 weeks prior to the experiment. Animals were fed AIN-76A diet (5% corn oil) and kept in plastic cages, 5 mice per cage. They were maintained under 12 h light/dark cycle, at 20°±2° C. and a relative humidity 50±10%. Mice were divided into 7 groups as shown in Table 1. Tea, EGCG, and caffeine solution were consumed as drinking water for 13 weeks. After consumption of test substances in drinking water for 2 weeks, mice were administered NNK by gavage (56 mol/kg b.w or 11.65 mg/kg b.w. in corn oil) 3 times weekly for 10 weeks. The daily water consumption was measured and weekly body weights were recorded. Food consumption was determined only for weeks 6 and 7 after NNK treatment began. One week after the last NNK treatment, all groups were given tap water until sacrifice. Mice were sacrificed 6 weeks after the last NNK administration. Lung adenomas were counted. Representative tissues were processed for histopathological examination of tumors. Statistical significance was determined by the 2-sample student's t-test.

Groups of 10 to 12 six-week female A/J mice were given 2% tea solution, EGCG solution, or water as drinking water for 5 weeks. The concentration of EGCG solution was identical to that used in the bioassay (560 ppm EGCG in water). Two weeks after these treatments, NNK was administered in corn oil by gavage at a dose of 112 μmol/kg b.w. or 23 mg/kg b.w. 3 times weekly for 3 weeks. This dose, 2 times that of the bioassay dose, facilitated the detection of elevated 8-OHdG levels in tissue DNA. Mice were sacrificed 2 h after last NNK administration and lung and liver DNA were isolated for the analysis of $O^6$-mG and 8-OH-dG.

In a separate but similar experiment, mice that drank water, green tea or EGCG solution of the same concentration as the above experiment were treated with NNK in corn oil by gavage (56 μmol/kg b.w. or 11.65 mg/kg b.w.) 3 times weekly for 3 weeks. Five mice were sacrificed from each group 4 and 24 h after the last NNK administration. Five mice of each group were sacrificed at these time points and the lung DNA was isolated for $O^6$-mG analysis.

DNA was isolated by a modified Marmur's procedure. Marmur, J. A procedure for the isolation of deoxyribonucleic acid from microorganisms. J. Mol. Biol., 3: 208–216, 1961. Briefly, individual lung and liver DNA in 6 or 8 ml cold 15 mM NaCl-50 mM trisodium citrate pH 7.0 buffer was homogenized. After centrifuging at 9000×g for 20 min, the pellet was dispersed in equal volume of 10 mM Tris-1 mM EDTA-1% sodium dodecyl sulfate, pH 7.0 buffer and incubated with 10 units of proteinase K at 37° C. for 10 min. The mixture was extracted twice with chloroform:isoamyl alcohol (24: 1, v:v). DNA was precipitated from the aqueous phase by adding 0.1 volume of 2M NaCl and 2 volumes of cold ethyl alcohol. DNA was redispersed in 10 mM Tris-HCl pH 7.0 buffer and RNA and protein were removed by digesting with ribonuclease A (10 unit) at 37° C. for 10 min followed by proteinase K (10 unit) for 30 min and extracted with chloroform:isoamyl alcohol. The precipitated DNA was kept at 20° C. overnight and was solubilized in 0.5 ml (lung) and 0.6 ml (liver) 10 mM Tris-HCl, pH 7.0 buffer. A portion of this DNA (0.2 ml) was immediately used for 8-OH-dG analysis. Statistical significance was determined by the 2-sample student's t-test.

For $O^6$-mG analysis, DNA was hydrolyzed with 0.1 N HCl at 80° C. for 60 min. The hydrolysate was filtered with Gelman Acrodisc to obtain samples for HPLC analysis as previously described. Chung, F. -L., Wang, M., and Hecht, S. S. Effects of dietary indoles and isothiocyanates on N-nitrosodimethylamine and 4-(methylnitrosamino)1-(3-pyridyl)1-butanone a-hydroxulation and DNA methylation in rat liver. Carcinogenesis, 6: 539–543, 1985.

For the 8-OH-dG analysis, 10 μl 10.5M sodium acetate, pH 5.1 buffer, was added to the DNA solution. DNA was then denatured by heating at 90°–95° C. for 2 min. An aliquot containing 100 to 200 μg DNA was incubated with nuclease $P_1$ at 37° C. for 1 h. After an addition of 40 μl 0.4M Tris-HCl, pH 7.5, the DNA was further digested with 8 units of alkaline phosphatase at 37° C. for 1 h. The resulting hydrolysate was centrifuged and the supernatant was stored at 0° C. prior to analysis by HPLC. The DNA samples were analyzed within 4 to 5 h after enzymatic hydrolysis.

In the present examination, NNK was given by gavage in 30 doses over a period of 10 weeks. Each dose was 11.65 mg/kg b.w. which equals a total NNK dose of 1.7 μmol/kg b.w. (350 mg/kg b.w.). This dose regimen induced a 100% tumor incidence with an average of 22.5 lung adenomas per mouse at week 16 after NNK treatment began. Table 1 shows the inhibitory effects of green tea, EGCG, and caffeine on the formation of lung adenomas in NNK-treated mice.

TABLE 1

Effect of Tea, EGCG and Caffeine on NNK-induced lung adenomas in A/J mice

| Treatment Group | % of Mice with Tumors | Number of Animals | Tumors/Mouse (±S.D.) |
|---|---|---|---|
| NNK | 100 | 30 | 22.5 ± 4.7 |
| Tea + NNK | 100 | 25 | 12.2 ± 4.3[a] |
| EGCG + NNK | 100 | 25 | 16.1 ± 5.3[a] |
| Caffeine + NNK | 100 | 15 | 19.2 ± 4.8[b] |
| Tea | 7 | 15 | 0.1 ± 0.2 |
| EGCG | 20 | 15 | 0.3 ± 0.6 |
| Caffeine | 20 | 15 | 0.3 ± 0.6 |

[a]Statistically different from NNK group, p < 0.001
[b]Statistically different from NNK group, p < 0.05

While the tumor incidences were not affected by green tea and EGCG, mice that drank tea or EGCG solution developed only an average of 12.2 tumors or 16.1 tumors per mouse. These tumor multiplicities correspond to a 45% and 30% reduction of lung tumor formation in these groups as compared with the NNK-treated group that drank water. Interestingly, the caffeine group also showed a marginal but significant inhibition. Groups that drank tea, EGCG, or caffeine without NNK treatment showed the tumor incidence and multiplicity comparable to the background levels commonly seen in the control groups of our previous studies. Chung, F. -L., Morse, M. A., and Eklind, K. I. New potential chemopreventive agents for lung carcinogenesis of tobacco-specific nitrosamine. Cancer Res., 52: in press, 1992.

Figure 2:
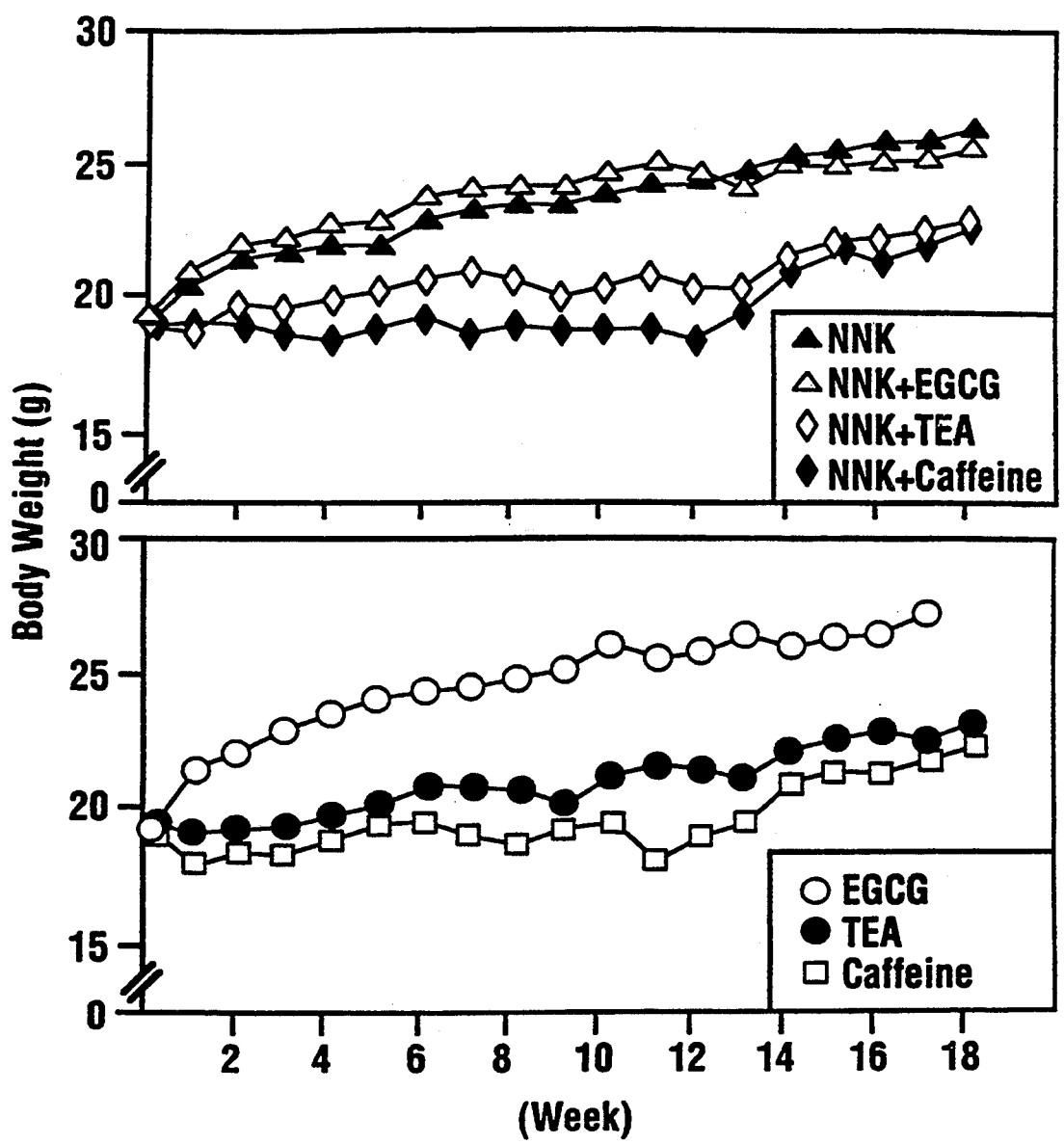
FIG. 2 shows the growth curves of mice during tumor bioassay.

FIG. 2 shows the body weight curves of different groups during bioassay. Independent of NNK treatment, groups that drank tea or caffeine solution showed consistently lower weight gains as compared with groups that drank water or EGCG solution. Since comparable body weight gains were observed in the tea and caffeine groups, it appears that caffeine is responsible for the decrease in weight gain in the tea group. In contrast to the tea and caffeine groups, mice that drank EGCG solution had normal growth. The weekly water consumption, 0.6–0.7 ml/g b.w., was similar among most of the groups, with the only exception of the tea group which consumed an average of 0.82 ml/g b.w. No difference in diet consumption between groups was found.

Multiple NNK doses resulted in an accumulation of $O^6$-mG in both lung and liver DNA. Table 2 shows that, 2 h after the last NNK treatment at a dose of 23 mg/kg b.w., levels of $O^6$-mG in mouse lung and liver were 55.3 and 107 μmol/mol guanine, respectively.

TABLE 2

Effect of green tea and EGCG on $O^6$-mG formation in lung and liver DNA of A/J mice 2 h after treatment with NNK[a]

| Treatment | No. of mice | $O^6$-mG (μmol/mol quanine) Lung | Liver |
|---|---|---|---|
| NNK | 10 | 55.3 ± 11.0[b] | 107.7 ± 29.8 |
| NNK + Tea | 12 | 57.6 ± 16.7 | 110.1 ± 38.2 |
| NNK + EGCG | 12 | 57.5 ± 12.3 | 94.2 ± 36.7 |

[a]Mice that drank water, green tea, or EGCG solution were administered NNK in corn oil (23 mg/kg b.w.) by gavage 3 times weekly for 3 weeks. Mice were sacrificed 2 h after the last NNK treatment.
[b]Mean ± S.D.

Despite the fact that $O^6$-mG is a critical lesion in NNK tumorigenesis in A/J mice (20–22), tea or EGCG solution given as drinking water before and during NNK adminstration exhibited little effect on the formation of this DNA lesion in either lung or liver. In a separate study, $O^6$-mG in lung DNA was measured at 4 and 24 h after NNK treatment.

TABLE 3

Effect of green tea and EGCG on $O^6$-mG levels in lung DNA of A/J mice 4 and 24 h after treatment with NNK[a]

| Treatment | $O^6$-mG (μmol/mol quanine) 4 h | 24 h |
|---|---|---|
| NNK | 16.8 ± 2.7[b] | 17.8 ± 6.2 |
| NNK + tea | 23.3 ± 2.8 | 19.2 ± 5.0 |
| NNK + EGCG | 19.6 ± 1.0 | 15.0 ± 5.5 |

[a]Mice that drank water, green tea, or EGCG solution were administered NNK in corn oil by gavage (11.65 mg/kg b.w.) 3 times weekly for 3 weeks. Mice were sacrificed 4 and 24 h after the last NNK treatment.
[b]Mean ± S.D. from 5 mice.

Table 3 shows that levels of $O^6$-mG were not significantly affected at both time points by green tea or EGCG treatment. In fact, a small increase of $O^6$-mG in the tea group was seen as compared with the NNK control group 4 h after NNK treatment. The small difference in $O^6$-mG levels between 4 and 24 h in both tea and EGCG group suggests that the $O^6$-mG methyl transferase activity was not altered by these treatments.

TABLE 4

Effect of green tea and EGCG on the 8-OH-dG levels in lung and liver DNA of A/J mice 2 h after treatment with NNK[a]

| Treatment | No. of Mice | 8-OH-dG/$10^5$ dG Lung | Liver |
|---|---|---|---|
| Control | 11 | 1.7 ± 1.2[b] | 3.9 ± 0.6 |
| NNK | 10 | 3.2 ± 1.7[c] | 4.7 ± 1.1 |
| NNK + tea | 11 | 1.9 ± 1.0[d] | 4.3 ± 1.4 |
| NNK + EGCG | 12 | 2.1 ± 1.1[e] | 4.3 ± 1.2 |
| EGCG | 10 | 1.8 ± 0.9[f] | 4.1 ± 1.2 |
| Tea | 11 | 1.8 ± 0.7[g] | 4.0 ± 1.4 |

[a]Mice that drank water, green tea, or EGCG solution as drinking water were administered NNK in corn oil (23 mg/kg b.w.) by gavage 3 times weekly for 3 weeks. Mice were sacrificed 2 h after the last NNK treatment.
[b]Mean ± S.D.
[c]Statistically different from control group, $p < 0.01$
[d]Statistically different from NNK group, $p < 0.05$
[e]Statistically different from NNK group, $p < 0.05$
[f]Statistically different from NNK group, $p < 0.01$
[g]Statistically different from NNK group, $p < 0.01$ Table 4 shows that multiple doses of NNK caused a significant increase in the 8-OH-dG levels in lung DNA from 1.7±1.2 to 3.2±1.7 adducts per $10^5$ dG, an approximately 2-fold elevation from the basal levels. Only a slight increase from 3.9±0.6 to 4.7±1.1 adducts per $10^5$ dG was seen in liver DNA. However, this increase was not statistically significant. Green tea and EGCG suppressed the elevated 8-OH-dG levels in lungs of NNK-treated mice. The decreased in 8-OH-dG levels in lungs of NNK-treated mice that drank green tea or EGCG is consistent with their inhibitory activity against lung tumor formation.

The results of this study showed that green tea has a protective effect against NNK-induced lung tumorigenesis in mammals and particularly in A/J mice. The polyphenol EGCG in green tea appears to be the major active component for this activity. Green tea is composed of at least 10 to 20% polyphenols. Graham, H. N. Tea, the plant and its manufacture, chemistry and consumption of the beverage. In: G. A. Spiller (ed.), The methylxanthine beverages and foods. Chemistry, Consumption and Health Effects, pp. 29–74. New York: Alan R. Liss, 1984. These compounds are powerful antioxidants, capable of scavenging $H_2O_2$ and the superoxide anion, thus preventing the formation and retention preventing oxygen free radical-induced cytotoxicity and mutagenicity. Rush, R. J., Cheng, S. J., and Klaunig, J. E. Prevention of cytotoxicity and inhibition of intercellular communication by antioxidant catechins isolated from Chinese green tea. Carcinogenesis, 10: 1003–1008, 1989. Osawa, T., Namiki, M., and Kawakishi, S. Role of dietary antioxidants in protection against oxidative damage. Basic Life Sci., 52: 139–153, 1990. Green tea polyphenol fractions have been shown to be protective in mice against skin tumor induction by polycyclic aromatic hydrocarbons. Wang, Z. Y., Khan, W. A., Bickers, D. R., and Mukhtar, H. Protection against polycyclic aromatic hyrocargon-induced skin tumor initiation in mice by green tea polyphenols. Carcinogenesis, 10: 411–415, 1989. It also inhibited aflatoxin $B_1$ hepatocarcinogenesis. Chen, Z. Y., Yan, P. Q., Qin, G. Z., and Qin, L. L. Effect of six edible plants on the development of $AFB_1$-induced s-glutamyl transpeptidase positive hepatocyte foci in rats. Chinese Journal Oncology, 9:109–111, 1987. The administration of several types of Chinese tea as drinking water resulted in a significant reduction in esophageal tumors induced by N-nitrosobenzylmethylamine. Han, C. and Xu, Y. The effect of Chinese tea on occurrence of esophageal tumor induced by N-nitrosomethylbenzylamine in rats. Biomedical and Environmental Science, 3: 35–42, 1990. Total green tea extract given orally also protected mice from UV-induced skin tumorigenesis. Wang, Z. Y., M.-T., Ferraro, T., Wong, C. Q., Newmark, H., Yang, C. S., and Conney, A. H. Inhibitory effect of orally administered green tea on ultraviolet B light (UV-B)-induced carcinogenesis in skin of SKH-1 mice. Proc. Amer. Assoc. Cancer Res., 1991. Because either tea or total tea polyphenol fraction was used in these studies, it was not possible to identify which are the active compounds in green tea responsible for the inhibitory effect. EGCG, the main polyphenol in green tea, is an antimutagen. the topical application of EGCG inhibited teleocidine promoted 7,12-dimethylbenz[a]anthracene-induced skin tumors in mice. More recently, the antipromoting activity of EGCG was demonstrated in mouse duodenum carcinogenesis induced by N-ethyl-N'-nitro-N-nitrosoguanidine.

Our results showed that EGCG, given in concentration identical to that found in tea infusion, inhibited NNK-induced lung tumorigenesis in mice. Furthermore, EGCG, unlike caffeine, exerted no adverse effect on growth. Therefore, it may be considered as a useful chemopreventive agent.

It is estimated that an average smoker is exposed to roughly 2 mg of NNK annually. Hoffman, D. and Hecht, S. S. Nicotine-derived N-nitrosamines and tobacco related cancer: current status and future directions. Cancer Res., 45: 935–944, 1985. In our bioassay, mice consumed an average of 100 mg of EGCG and at the same time were exposed to 7 mg of NNK (EGCG/NNK ratio 14.3).

In the tea preparation used in the present study, caffeine constitutes about 5.6% of tea leaves by dry weight. It is a major component in tea and has been shown to inhibit chemical carcinogenesis in other studies. The exact mechanisms by which caffeine inhibits the induction of tumors are not clear. Recently, Lagopoulos, et al found that the reduced body weight gains in caffeine-treated groups correlated with decreased hepatocarcinogenesis by diethylnitrosamine. VanderPloeg et al suggested that the inhibition of DMBA-induced mammary gland tumorigenesis in rats by caffeine was due to its ability to suppress its metabolism. In the present study although diet consumption appeared unaffected by caffeine treatment, the body weight gains in the caffeine group were considerably lower than those in the EGCg and NNK control groups. Therefore, the slight but significant reduction in lung tumor multiplicity by caffeine treatment could be related to its negative effect on body weight. Regardless of the mechanism, the potential protective effect of caffeine should not be ignored because of its widespread consumption by humans.

Several lines of evidence indicated that $O^6$-mG is a critical lesion in NNK lung tumorigenesis. Belinsky, S. A., Foley, J. F., White, C. M., Anderson, M. W., and Maronpot, R. R. Dose-response relationship between $O^6$-methylguanine formation in Clara cells and induction of polmonary neoplasia in the rat by 4-(methylnitrosamino)-1-(3-pyridyl)-1-butanone. Cancer Res., 50: 3772–3780, 1990. Peterson, L. A. and Hecht, S. S. $O^6$-Methylguanine is a critical determinant of 4-(methylnitrosamino)-1-(3-pyridyl)-1-butanone tumorigenesis in A/J mouse lung. Cancer Res., 51: 5557–5564, 1991. Devereux, T. R., Anderson, M. W., and Belinsky, S. A. Role of ras protooncogene activation in the formation of spontaneous and nitrosamine-induced lung tumors in the resistant C3H mouse. Carcinogenesis, 12: 299–303, 1991. Previously we showed that a decrease in lung $O^6$-mG formation correlated with a decrease of lung tumor formation in NNK-treated A/J mice pretreated with arylalkyl isothiocyanates or indole-3-carbinol. In the present study, however, neither green tea nor EGCG treatment inhibited NNK-induced $O^6$-mG formation or stimulated its repair, although both treatments inhibited the lung tumor induction by NNK. These results suggested that additional mechanisms other than DNA methylation or repair are likely to be involved in lung tumorigenesis by NNK. NNK treatment also resulted in pyridyloxobutylation of DNA. However, the exact role of this adduct in NNK lung tumorigenesis is not yet known. Our results showed that multiple NNK doses caused a significant increase in 8-OH-dG levels in the lung but not in the liver. The elevation of this lesion in lung DNA was suppressed by green tea treatment. Since 8-OH-dG is a DNA lesion cause by oxidative stress commonly associated with tumor promotion, these results suggest that the inhibition of lung tumor induction by green tea could be due in part to antipromoting activity of its polyphenols and particularly EGCG. The antioxidants ellagic acid and butylated hydroxyanisole (BHA) given in the diet inhibited lung adenoma formation in NNK-treated A/J mice. Together with these results, the present study provides evidence supporting the role of green tea and its major polyphenol EGCG as antioxidants in the inhibition of NNK lung tumorigenesis.

There may be many modifications and variations of the methods and compounds set forth hereinabove. These modifications and variations will not depart from the scope of the invention, if defined by the following claims and equivalents thereof.

What is claimed:

1. A method for treating NNK-induced lung tumor formation in a mammal in need thereof comprising administering to said mammal a pharmacologically effective amount of epigallocatechin gallate (EGCG).

2. A method as claimed in claim 1, wherein the EGCG is administered to the mammal in a composition which is substantially free of caffeine.

3. A method as claimed in claim 2, wherein the composition is administered to the mammal in the form of a solution in water.

4. A method as claimed in claim 2, wherein the composition consists essentially of EGCG and water.

* * * * *